Figure 1:
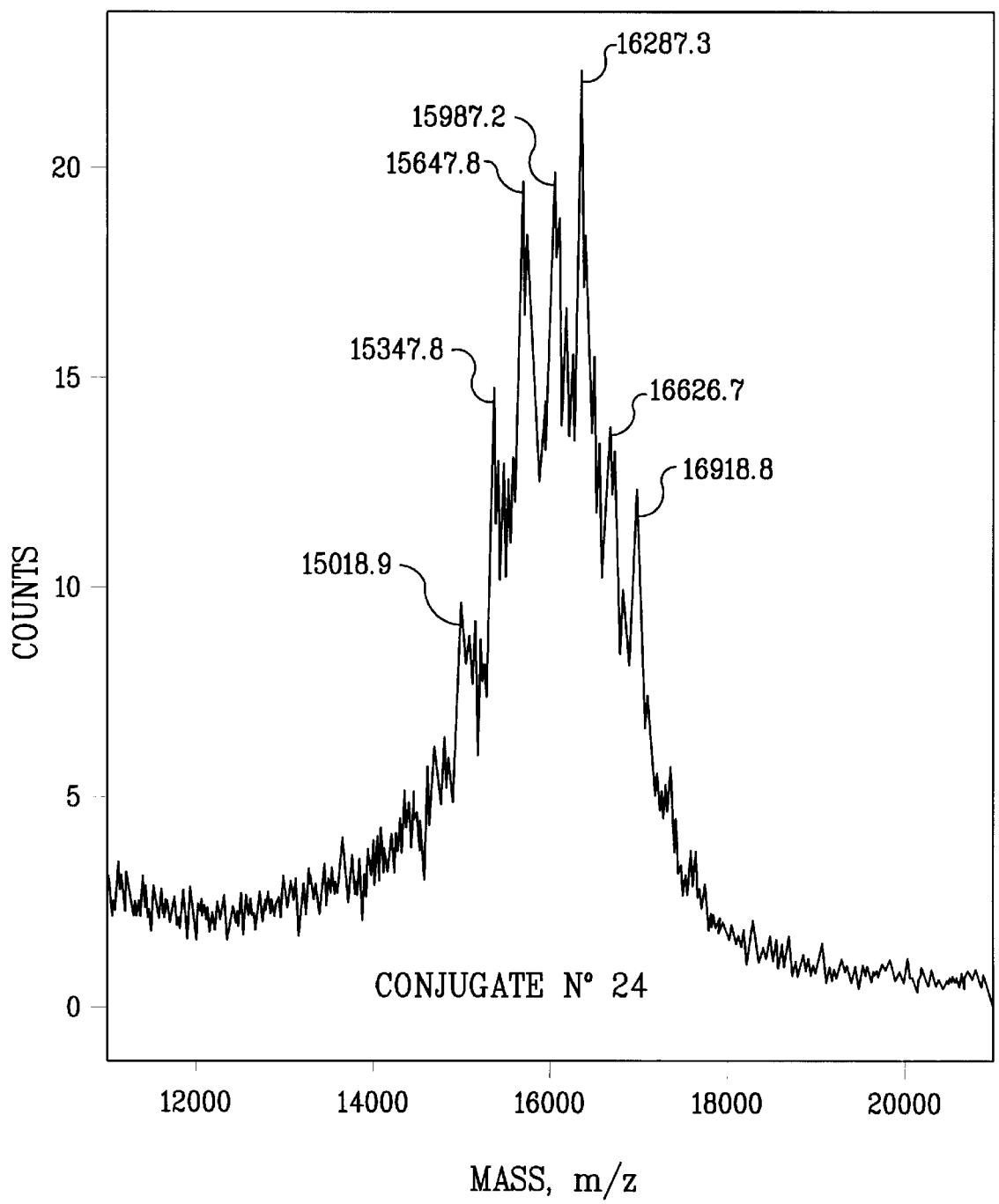

United States Patent [19]

Aspe

[11] Patent Number: 6,120,987
[45] Date of Patent: Sep. 19, 2000

[54] NON-AGGREGATED FLUORESCENT CONJUGATES AND THE PROCESS FOR THEIR PREPARATION

[75] Inventor: Daniel Aspe, Laudun, France

[73] Assignee: Cis bio International, Cernay, France

[21] Appl. No.: 09/095,471

[22] Filed: Jun. 10, 1998

Related U.S. Application Data

[63] Continuation-in-part of application No. PCT/FR97/02288, Dec. 12, 1997.

[51] Int. Cl.[7] .............................. C12Q 1/00; C07H 21/02
[52] U.S. Cl. ............................ 435/4; 536/25.32; 536/51; 548/465; 548/467; 548/469; 436/800
[58] Field of Search ..................... 435/4, 6, 7.2; 436/800; 536/25.32, 51; 548/465, 467, 469; 424/9.6

[56] References Cited

U.S. PATENT DOCUMENTS

| | | | |
|---|---|---|---|
| 5,068,227 | 11/1991 | Weinshenker | 514/58 |
| 5,268,486 | 12/1993 | Waggoner et al. | 548/427 |
| 5,627,027 | 5/1997 | Waggoner | 435/6 |
| 5,661,040 | 8/1997 | Huff et al. | 436/531 |

FOREIGN PATENT DOCUMENTS

| | | |
|---|---|---|
| WO91/02040 | 2/1991 | WIPO. |
| WO91/05605 | 5/1991 | WIPO. |
| WO91/02700 | 1/1995 | WIPO. |

OTHER PUBLICATIONS

International Search Report dated Mar. 11, 1998 issued in PCT Application No. PCT/FR97/02288 filed Dec. 12, 1997.

*Primary Examiner*—John Kight
*Assistant Examiner*—Charanjit S. Aulakh
*Attorney, Agent, or Firm*—Woodcock Washburn Kurtz Mackiewz & Norris LLP

[57] ABSTRACT

The invention relates to a process for the preparation of a fluorescent conjugate between a carrier molecule possessing at least one amino, hydroxyl, carboxyl and/or sulfhydryl group and a fluorophoric reagent possessing at least one functional group capable of reacting with said amino, hydroxyl, carboxyl and/or sulfhydryl group(s), which consists in bringing said carrier molecule and said fluorophoric reagent into contact with an aqueous solution of a water-soluble macrocycle.

The invention further relates to the conjugates obtained by this process and to their use.

24 Claims, 3 Drawing Sheets

NON-AGGREGATED FLUORESCENT CONJUGATES AND THE PROCESS FOR THEIR PREPARATION

This is a continuation-in-part application of International patent application No. PCT/FR97/02288 filed Dec. 12, 1997.

The invention relates to a process for the manufacture of non-aggregated fluorescent conjugates. The invention further relates to the non-aggregated fluorescent conjugates obtained by this process and to their use as fluorescent tracers.

The autoaggregation of hydrophobic dyes such as thionine or methylene blue is well known in aqueous solution at high concentration, as described in J. Am. Chem. Soc. 63, 69 (1941). These aggregates cause a change in the absorption spectrum and a reduction in the fluorescence of said dyes.

Cyanins are also known to aggregate, causing a quenching of fluorescence (J. Phys. Chem. 69, 1894 (1965)).

This aggregation phenomenon is particularly exacerbated in the manufacture of fluorescent conjugates. Thus Waggoner et al. have observed an aggregation phenomenon following the conjugation of cyanin isothiocyanate with an antibody (Cytometry 10, 11–19 (1989)). These same authors describe cyanin arylsulfonates which have the particular characteristic of coupling via N-hydroxysuccinimide and of aggregating weakly on protein conjugates, a property which said authors attribute to the presence of sulfonate groups on the cyanin ring (U.S. Pat. No 5,268,486), as well as cyanins based on naphthalenesulfonate (Bioconjugate Chemistry 7, 356–362 (1996)). In the latter article, the authors show the importance of the number of sulfonates in the disaggregation processes.

However, it has been reported that the fluorescence of a conjugate between a cyanin designated by CY5.18, disclosed in U.S. Pat. No. 5,268,486, and an anti-HCG antibody (molar ratio=1.7) is quenched in comparison with that of the free cyanin (Anal. Biochem. 217, 197–204 (1994)).

Furthermore, the Applicant has performed experiments on anti-prostate cancer and anti-thyroid specific hormone antibodies labeled with the compounds CY5.18 and CY5.29, disclosed in the same U.S. Pat. No. 5,268,486 (Examples 1 and 2). These Examples show a strong quenching of the cyanins irrespective of the final degree of labeling.

Finally, in the same U.S. Pat. No. 5,268,486, the authors underline the importance of cyanins as a potential replacement for phycobiliproteins and emphasize the following advantages:

stability lower cost simplified labeling procedure size suitable for the recognition of small molecules.

However, these advantages become ineffectual when the cyanins are found to be aggregated on the conjugates.

To mitigate the disadvantage of the aggregation of cyanins, patent application WO 96/00902 proposes the introduction of iminium groups into their structure. However, said patent application limits itself to an assessment of the disaggregating capacity of structures described therein by comparing the UV spectra in saline solutions of low and high concentration, and gives no results pertaining to the conjugates.

In the same way, the increase in fluorescence caused by the addition of cyclodextrin to a medium containing a fluorophore is described in the literature (J. Chromatog. 452 (1988); Macromolecules 10(3), 676–681 (May–June 1977)).

Conversely, some fluorescent molecules are quenched by the addition of cyclodextrins (Journal of Inclusion Phenomena and Molecular Recognition in Chemistry 18, 385–396 (1994), Kluwer Academic Publishers).

The formation of cyanin-cyclodextrin inclusion complexes is described in the literature (J. Am. Chem. Soc. 112, 5824–5830 (1990)). Depending on the conditions and the nature of the cyclodextrin, it is possible to see monomeric or dimeric complexes, which favor the aggregation of the cyanins and hence the quenching of their fluorescence.

To preserve the fluorescent properties of the inclusion complexes, the prior art describes covalent bonds involving a functional group of the cyclodextrin (WO 91/02040).

Patent application WO 91/01090 describes europium chelates covalently attached to a cyclodextrin, which is then coupled to a protein.

However, this type of bond is difficult to produce, in particular because it requires chemical modification of the cyclodextrin (for example in the form of N-hydroxysuccinimide, maleimide, a thiol or an amine) and has the following disadvantages:

it degrades the properties of the inclusion complexes and hence detracts from the fluorescence performance characteristics;

it degrades the properties of the protein by labeling the cyclodextrin on bioavailable functional groups.

The present invention proposes to overcome these disadvantages and to preserve the properties of conjugates between a carrier molecule and a fluorophoric reagent.

Thus a first object of the invention consists in obtaining a highly fluorescent and non-aggregated conjugate.

A further object of the invention consists in obtaining said fluorescent conjugate in a simple and rapid manner.

According to a first aspect of the invention, these objects are achieved by a process for the preparation of a fluorescent conjugate between a carrier molecule possessing at least one amino, hydroxyl, carboxyl and/or sulfhydryl group and a fluorophoric reagent possessing at least one functional group capable of reacting with said amino, hydroxyl, carboxyl and/or sulfhydryl group(s), which consists in bringing said carrier molecule and said fluorophoric reagent into contact with an aqueous solution of a water-soluble macrocycle containing from 1 to 40% (w/v) of said macrocycle.

The reaction mechanism can be represented by the following scheme:

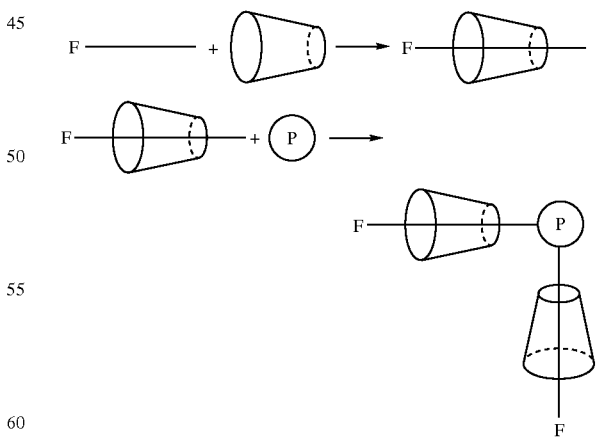

in which:

F is the fluorophoric reagent and

P is the carrier molecule.

The carrier molecule P reacts with the functional groups of the fluorophoric reagent F. This has the effect of preserving the intermolecular distances and preventing the fluorophoric reagents from coming closer together on the carrier molecule, the consequence being to reduce the aggregation of the fluorophoric reagents.

The concentration of macrocycle in the aqueous solution of macrocycle is advantageously between 10 and 40% (w/v).

The water-soluble macrocycle used will advantageously be an optionally substituted cyclodextrin or a calixarene substituted by hydrophilic groups.

α-Cyclodextrin, β-cyclodextrin, γ-cyclodextrin, hydroxypropyl-α-cyclodextrin, hydroxypropyl-β-cyclodextrin, hydroxypropyl-γ-cyclodextrin, hydroxyethyl-α-cyclodextrin, hydroxyethyl-β-cyclodextrin, hydroxyethyl-γ-cyclodextrin or 2,6-di-O-methylheptakis-β-cyclodextrin may be mentioned as examples of cyclodextrins which can be used in the process according to the invention.

The calixarenes which can be used in the process according to the invention have the structure

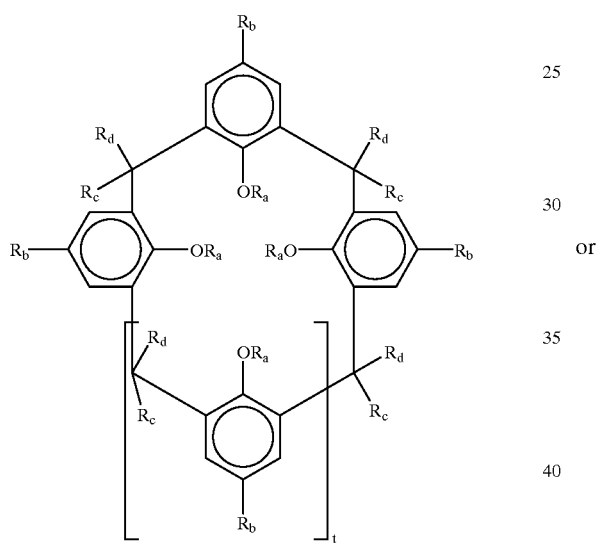

in which:

$R_a$ and $R_b$ are each a hydrophilic group selected from H, $(CH_2)_pCO_2H$, $(CH_2)_pOH$, $(CH_2)_pNH_2$, $(CH_2)_pSO_3H$ and $(CH_2)_pN^+R_cR_dR_e$;

$R_c$, $R_d$ and $R_e$ are each hydrogen or a $(C_1-C_3)$alkyl;

p varies from 0 to 4 for $R_b$ and from 1 to 4 for $R_a$; and t varies from 1 to 5.

The water-soluble macrocycle forms an inclusion complex, either with the fluorophoric reagent or with the carrier molecule, and thus forms a stable rotaxane structure. This inclusion complex can remain in the final structure of the fluorescent conjugate obtained by the process according to the invention.

In general the fluorophoric reagent used is a chromophore containing one or more aromatic rings, said chromophore having a high molecular extinction coefficient of more than 20,000, preferably of more than 50,000.

According to one preferred aspect of the invention, said fluorophoric reagent is selected from:

*a cyanin of the structure

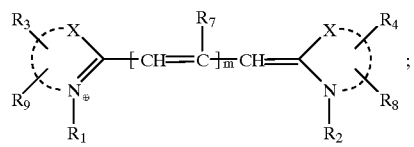

*a hemicyanin of the structure

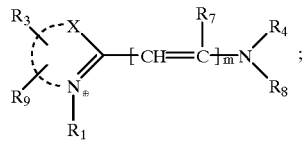

*a merocyanin of the structure

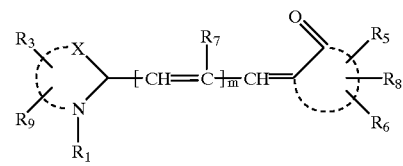

or

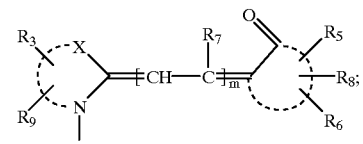

*a styryl compound of the structure

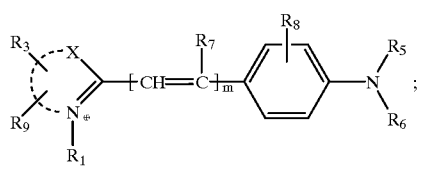

*a rhodamine of the structure

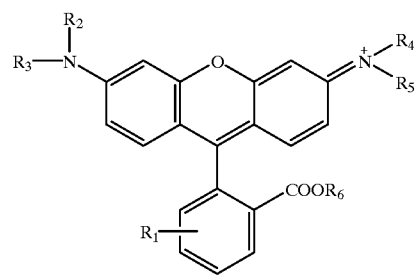

or

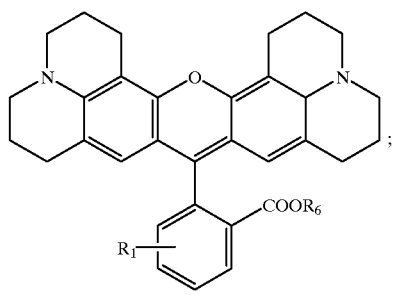

*a fluorescein of the structure

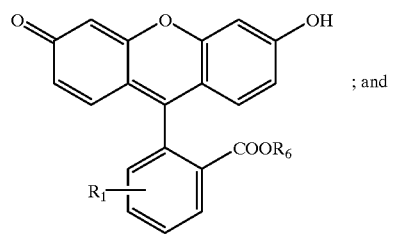
; and

*a naphthofluorescein of the structure

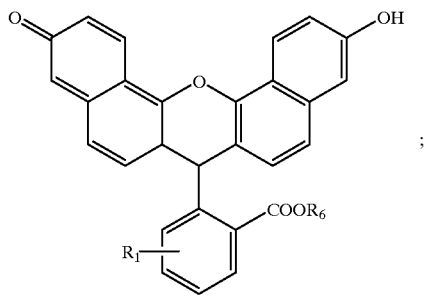
;

in which structures:

the broken lines each represent the carbon atoms required to form 1 to 3 fused rings, the groups $R_3$, $R_4$, $R_5$, $R_6$, $R_8$ and $R_9$ being attached to these rings;

- X and Y are each N, , O, S or $C(CH_3)_2$;

m has a value of 1, 2, 3 or 4;

at least one of the groups $R_1$ to $R_7$ is capable of reacting with an amino, hydroxyl, carboxyl and/or sulfhydryl group and is selected from:

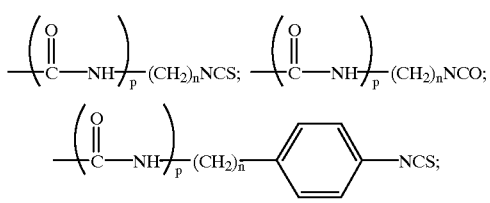

-continued

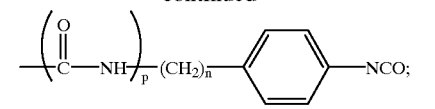

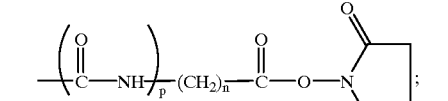

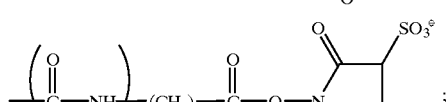

$$-\left(\overset{O}{\underset{\|}{C}}-NH\right)_p-(CH_2)_n-N$$

$$-\left(\overset{O}{\underset{\|}{C}}-NH\right)_p-(CH_2)_n-S-S-Ar;$$

$$-\left(\overset{O}{\underset{\|}{C}}-NH\right)_p-(CH_2)_n-NH-Ar;$$

$$-\left(\overset{O}{\underset{\|}{C}}-NH\right)_p-(CH_2)_n-N_3;$$

$$-\left(\overset{O}{\underset{\|}{C}}-NH\right)_p-(CH_2)_n-\phantom{X}-N_3;$$

$$-\left(\overset{O}{\underset{\|}{C}}-NH\right)_p-(CH_2)_n-NH_2 \text{ and } -\left(\overset{O}{\underset{\|}{C}}-NH\right)_p-(CH_2)_n-SH$$

in which n varies from 0 to 8, p is equal to 0 or 1 and Ar is a 5- or 6-membered heterocycle comprising 1 to 3 heteroatoms which is optionally substituted by a halogen atom, those of the groups $R_1$ to $R_7$ which do not represent one of the above reactive entities being selected from hydrogen and a group $-(CH_2)_r-Z$, in which r varies from 0 to 4 and Z is a group $CH_3$, $SO_3H$, OH or $N^+R_1R_2R_3$, in which $R_1$, $R_2$ and $R_3$ are as defined above, and at least one of the groups $R_8$ and $R_9$ is a group $SO_3^-$ or $SO_3H$, the other group being hydrogen or a group $SO_3^-$ or $SO_3H$. p is preferably equal to 0 in the above formulae.

More particularly, a cyanin of the structure $$R_3 \underset{R_9}{\overset{X}{\diagdown}} \underset{R_1}{\overset{R_7}{\diagdown}} CH=\overset{R_7}{C}_m CH \underset{R_2}{\overset{Y}{\diagdown}} \underset{R_8}{\overset{R_4}{\diagdown}}$$

in which the groups $R_1$, $R_2$, $R_3$, $R_4$, $R_7$, $R_8$ and $R_9$ are as defined above, will advantageously be used.

A preferred class of cyanins consists of the above cyanins in which X and Y are each a group $C(CH_3)_2$.

Among these cyanins, those in which:

(i) $R_1$ and $R_2$ are each a 5-(succinimidooxycarbonyl)pentyl group; $R_3$, $R_4$ and $R_7$ are each hydrogen; $R_8$ and $R_9$ are each a sulfonate group; and m is equal to 2; or (ii) $R_1$ is a 5-(succinimidooxycarbonyl)pentyl group; $R_2$ is an ethyl; $R_3$, $R_4$ and $R_7$ are each hydrogen; $R_8$ and $R_9$ are each a sulfonate group; and m is equal to 2, are preferred.

The carrier molecule possessing at least one amino, hydroxyl, carboxyl and/or sulfhydryl group is a biomolecule intended in general for diagnosis or detection. This biomolecule may itself be used for the labeling of other molecules, especially proteins. Examples which may be mentioned are an antibody, an antigen, a protein, a peptide, a hapten, a lectin, avidin, streptavidin, ribonuclease, a toxin, a carbohydrate, an oligosaccharide, a polysaccharide, a nucleic acid, a hormone, a drug, a polymer, a polymeric particle, glass, a glass particle or a glass or polymer surface.

The process according to the invention has the following advantages:

it avoids the functionalization of cyclodextrins, thereby affording a saving of time and money;

it permits the irreversible stabilization of the inclusion complex between the water-soluble macrocycle and the fluorophoric reagent (inclusion complexes usually have low equilibrium constants);

it makes it possible to avoid quenching of the fluorescence of the conjugates obtained, without affecting the chemical structure of the fluorophoric reagent. In fact, the complexing properties of the water-soluble macrocycle permit a distancing in situ of the fluorophoric reagents, whose intermolecular distances are maintained after conjugation and purification of the conjugate. This distancing of the fluorophoric reagents on the carrier molecule avoids the phenomenon of aggregation and hence quenching of the fluorescence.

According to another aspect, the invention further relates to the fluorescent conjugates obtained by the process described above.

If the inclusion complex formed by the water-soluble macrocycle with the fluorophoric reagent and the carrier molecule remains in the final structure of the fluorescent conjugate, the fluorophoric reagent is bonded to the carrier molecule in such a way that the hydrophobic part of the fluorophoric reagent passes through the water-soluble macrocycle.

If the carrier molecule P and the fluorophoric reagent F are bulky groups, the complex produced will be stable and will form a rotaxane:

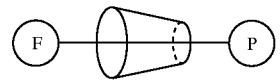

The complex obtained is novel because the cyclodextrin contains no covalent bonds with the fluorophoric reagent or the carrier molecule.

As indicated above, the fluorescent conjugates according to the invention, especially the rotaxane complexes, exhibit no quenching of fluorescence because of the distancing of the fluorophoric reagents on the carrier molecule.

The fluorescent conjugates according to the invention prove to be excellent fluorescent tracers.

Thus, according to another aspect, the invention relates to the use of the above-described fluorescent conjugates as fluorescent tracers. These tracers are applicable for example in fluorescence microscopy, in flow cytometry or in fluorescence immunodiagnosis, preferably in fluorescence microscopy or in flow cytometry. The fluorescent conjugates of the invention can also be used for the detection and/or determination, by fluorescence, of an analyte in a medium which may contain it.

The invention will be understood more clearly with the aid of the Examples below, which are given purely by way of illustration.

EXAMPLE 1

Manufacture of the Conjugates and UV Analysis

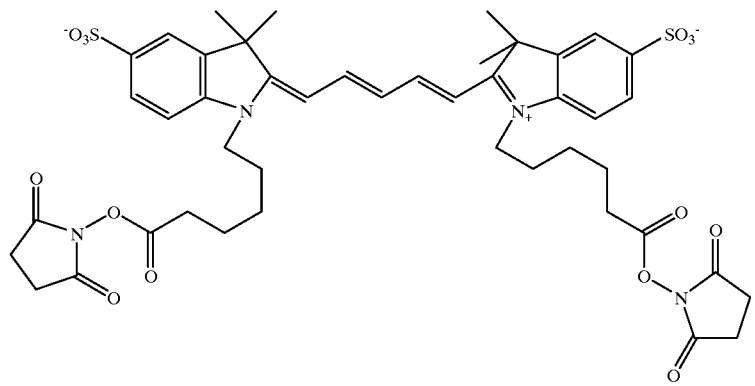

structure 1 structure 2

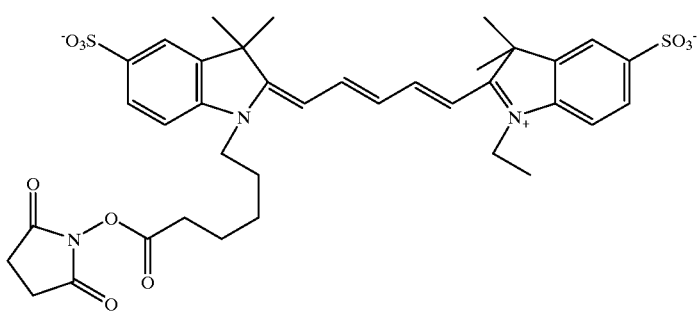

structure 3

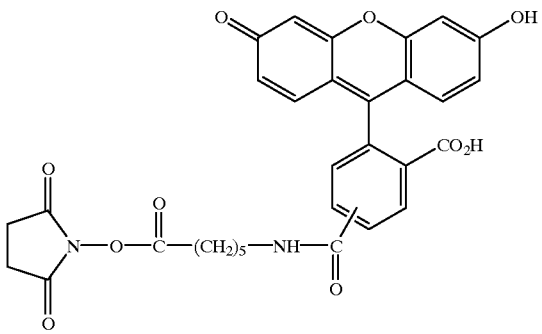

structure 4

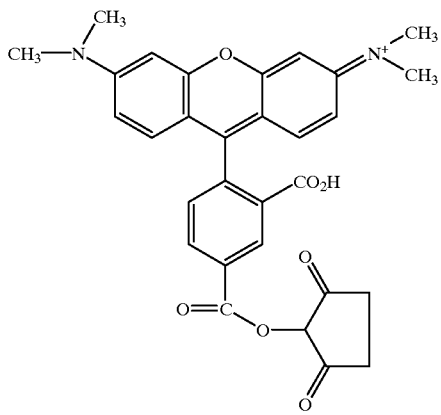

1/Influence of the Presence of Cyclodextrin

Conjugate No. 1

A sample containing 1 mg/ml of pancreatic tumoral marker antibody (reference: CA 19-9) in 0.1 M carbonate buffer of pH 9 is mixed at room temperature with a 17/1 molar excess of sulfoindodicarbocyanin of structure 1. After two hours the sample is purified by filtration on Sephadex® G25 gel.

The final molar ratio cyanin/antibody is 3.90.

UV lines are observed at 650 and 605 nm. The ratio $OD_{650}/OD_{605}$ is 1.62. The appearance of the 605 nm line indicates aggregation and quenching of the fluorescent molecule.

Conjugate No. 2

A 0.1 M carbonate buffer solution of pH 9 is prepared and 40% (w/v) of hydroxypropyl-β-cyclodextrin is dissolved therein.

The antibody used in the preparation of conjugate no. 1 is dialyzed in this buffer, to which a solution of the sulfoindodicarbocyanin of structure 1 is added.

The initial molar ratio cyanin/antibody is 17/1.

After two hours the sample is purified on Sephadex® G25 gel.

Lines are observed at 650 and 605 nm in UV analysis.

A final molar ratio cyanin/antibody of 5.89 and a ratio $OD_{650}/OD_{605}$ of 3.18 are obtained.

This Example clearly shows that the use of the cyanin-cyclodextrin complex made it possible to avoid the aggregation phenomenon found in the case of conjugate no. 1.

Conjugate No. 3

An anti-PSA antibody (PSA=Prostate Specific Antigen) is dialyzed in 0.1 M carbonate buffer of pH 9.

The solution containing 0.85 mg/ml of antibody is brought into contact with the sulfoindodicarbocyanin of structure 1. The initial molar ratio cyanin/antibody is 15/1.

After two hours the sample is purified on Sephadex® G25 gel.

The product is analyzed by UV. Lines are observed at 650 and 605 nm. A final molar ratio cyanin/antibody of 4.54 and a ratio $OD_{650}/OD_{605}$ of 1.40 are obtained.

Conjugate No. 4

The procedure is as described for the preparation of conjugate no. 3, except that 15% (w/v) of hydroxypropyl-β-cyclodextrin is added to the 0.1 M carbonate buffer of pH 9.

The conjugate gives the following results in UV analysis:
$OD_{650}/OD_{605}=2.60$
final molar ratio cyanin/antibody=0.96

A large increase in the ratio $OD_{650}/OD_{605}$ is observed in comparison with conjugate no. 3. This represents an important reduction in aggregation and substantially reduced quenching.

Conjugates No. 5 and 6

The procedure is as for conjugates no. 1 and 2 respectively, using an anti-chorionic gonadotropic hormone antibody at a concentration of 3 mg/ml and, as the fluorescent marker, the fluorescein of structure 3. The coupling pH is 9 and the incubation time is 30 min.

Lines are observed at 497 and 462 nm in UV analysis. The results are collated in Table 1:

TABLE 1

| Conjugate no. | Initial molar ratio fluorescein/antibody | Final molar ratio fluorescein/antibody | % cyclodextrin | $OD_{497}/OD_{462}$ |
|---|---|---|---|---|
| 5 | 4 | 2.1 | 0 | 2 |
| 6 | 10 | 2.4 | 40 | 2.3 |

The presence of cyclodextrin during the coupling of the fluorescein derivative made it possible to increase the optical density ratio $OD_{497}/OD_{462}$ and hence to reduce the aggregation phenomenon. (The UV spectrum of the fluorescein derivative by itself has a line ratio of 2.4.).

Conjugate no. 6 performs better in terms of fluorescence.

2/Influence of the Nature of the Cyclodextrin

Different cyclodextrins (conjugates 7 to 12) are tested in order to assess the influence of the nature of the cyclodextrin on the appearance of the spurious lines: 605 nm for the cyanin and 522 nm for the rhodamine. Two reference conjugates (conjugates no. 13 and 14) not containing cyclodextrin are also tested by way of comparison.

Conjugates 7 to 10 and 13 are obtained by the procedure described for the preparation of conjugate no. 2, applying the following experimental conditions:

nature of the antibody: anti-PSA antibody
concentration of the antibody: 0.75 mg/ml
concentration of the cyclodextrin in the 0.1 M carbonate buffer of pH 9:13 (or 0) % (w/v)
initial molar ratio cyanin/antibody: 17/1
incubation time: 2 h After two hours the free cyanin is extracted on an Amicon cone by centrifugation for 5 min at 4000 g. The sample is then purified on Sephadex® G25 gel.

Conjugates 11, 12 and 14 are obtained by the procedure described for the preparation of conjugate no. 2, applying the following experimental conditions:

fluorescent marker: rhodamine of structure 4 nature of the antibody: anti-chorionic gonadotropic hormone antibody concentration of the antibody: 4 mg/ml concentration of the cyclodextrin in the 0.1 M carbonate buffer of pH 9:10 (or 0) % (w/v)

initial molar ratio rhodamine/antibody: 17/1 incubation time: 30 min

The results are collated in Table 2:

TABLE 2

| | Conjugate no. 7 hydroxypropyl-α-cyclodextrin | Conjugate no. 8 hydroxypropyl-γ-cyclodextrin | Conjugate no. 9 hydroxypropyl-β-cyclodextrin | Conjugate no. 10 dimethyl-β-cyclodextrin | Conjugate no. 11 hydroxypropyl-β-cyclodextrin | Conjugate no. 12 dimethyl-β-cyclodextrin | Conjugate no. 13 — | Conjugate no. 14 — |
|---|---|---|---|---|---|---|---|---|
| final molar ratio cyanin (rhodamine)/antibody | 1.8 | 1.8 | 1.2 | 2.0 | 1 | 1.2 | 2.6 | 1.3 |
| $OD_{650}/OD_{605}$ * $OD_{533}/OD_{522}$ | 1.9 | 2.0 | 2.6 | 2.55 | 2.4* | 1.54* | 1.45 | 1.37* |
| fluorophore | cyanin | cyanin | cyanin | cyanin | rhodamine | rhodamine | cyanin | rhodamine |

The high values of the ratio $OD_{650}/OD_{605}$ (2.6 and 2.55) obtained with the two β-cyclodextrins show their capacity to disaggregate the cyanin of structure 1. These values also reflect high stability constants.

For the rhodamine derivative of structure 4, the use of hydroxypropyl-β-cyclodextrin makes it possible substantially to increase the optical density ratio and consequently to reduce the aggregation effect.

3/Influence of the Coupling Concentration

The concentrations are an important factor in the aggregation phenomena.

Different concentrations of antibody are therefore tested.

The conjugates are obtained by the procedure described for the preparation of conjugate no. 2, applying the following experimental conditions:

nature of the antibody: anti-PSA antibody
initial molar ratio cyanin/antibody: 17/1
coupling time: 2 h
nature of the cyclodextrin: dimethyl-β-cyclodextrin
concentration of cyclodextrin in the 0.1 M carbonate buffer of pH 9:13% (w/v)

The results are collated in Table 3:

TABLE 3

| | Conjugate no. 15 | Conjugate no. 16 | Conjugate no. 17 |
|---|---|---|---|
| concentration of antibody (mg/ml) | 0.75 | 1.5 | 3.0 |
| final molar ratio cyanin/antibody | 1.2 | 1.8 | 2.3 |
| $OD_{650}/OD_{605}$ | 2.7 | 2.6 | 2.45 |

With a concentration of 3 mg/ml, a high final molar ratio cyanin/antibody (2.3) is obtained with a good ratio $OD_{650}/OD_{605}$ (2.45).

These values should be compared with those in Table 2, where a final molar ratio cyanin/antibody of 2.6 is associated with a low ratio $OD_{650}/OD_{605}$ (1.45).

The process according to the invention therefore makes it possible to increase the final molar ratio cyanin/antibody while at the same time preserving a good ratio $OD_{650}/OD_{605}$.

This is not possible without the use of cyclodextrins.

4/Influence of the Concentration of Cyclodextrin

The conjugates are obtained by the procedure described for the preparation of conjugate no. 2, applying the following experimental conditions:

nature of the antibody: anti-TSH antibody (TSH=Thyroid Stimulating Hormone)

initial molar ratio cyanin (of structure 2)/antibody: 17/1 coupling time: 1 h nature of the cyclodextrin: hydroxypropyl-β-cyclodextrin

After extraction on an Amicon cone, the conjugate is purified on Sephadex® G25 gel.

The results are collated in Table 4:

TABLE 4

|  | Conjugate no. 18 | Conjugate no. 19 | Conjugate no. 20 |
| --- | --- | --- | --- |
| concentration of cyclodextrin (w/v) | 5% | 14% | 32% |
| final molar ratio cyanin/antibody | 3.9 | 2.74 | 2.45 |
| $OD_{650}/OD_{605}$ | 1.7 | 2.2 | 2.6 |

Table 4 clearly shows the influence of the percentage of cyclodextrin.

The law of mass action is displaced in the direction of formation of the complex by increasing the concentration of cyclodextrin.

EXAMPLE 2

Fluorescence Performance Characteristics of the Conjugates

The chosen analyte is PSA.

The measurements are made on a PERKIN-ELMER LS50 fluorimeter ($\lambda$max of emission=660 nm).

Two media are tested:

medium 1: 0.1 M phosphate buffer of pH 7 medium 2: medium 1+⅓ newborn calf serum

Conjugate no. 21 was manufactured by the procedure described for the preparation of conjugate no. 2.

Conjugates no. 22 and 23 were manufactured by the procedure described for the preparation of conjugate no. 1, but with antibody concentrations of 0.1 and 0.3 mg/ml respectively.

The results are collated in Table 5:

TABLE 5

|  | fluorescence units (a) | | | | | |
| --- | --- | --- | --- | --- | --- | --- |
|  | medium 1 | | medium 2 | | | |
|  | excitation 600 nm | excitation 650 nm | excitation 600 nm | excitation 650 nm | final molar ratio cyanin/antibody | $OD_{650}/OD_{605}$ |
| Conjugate no. 21 | 1 | 1 | 0.97 | 1.1 | 0.85 | 2.94 |
| Conjugate no. 22 | 0.12 | 0.26 | 0.13 | 0.28 | 1.0 | 2.5 |
| Conjugate no. 23 | 0.4 | 0.69 | 0.44 | 0.74 | 3.0 | 2.0 |

(a) The fluorescence units are expressed:
- in optical density units
- relative to conjugate no. 21 in medium 1.

An examination of Table 5 shows all the advantages of the process according to the invention:

in all cases the conjugate manufactured with the complex cyanin+cyclodextrin (conjugate no. 21) is superior in terms of fluorescence to the conjugates manufactured with cyanin and no cyclodextrin (conjugates no. 22 and 23);

in the presence of serum, there is no quenching of the conjugates manufactured.

EXAMPLE 3

Performance in an Immunoassay

The immunoassay is performed by the homogeneous method described by G. Mathis in Clin. Chem., vol. 39, no. 9, 1993.

The performance characteristics of conjugates 21, 22 and 23 were compared with one another using standard samples containing different concentrations of antigen.

The results are collated in Table 6:

TABLE 6

|  | Conjugate no. 21 | Conjugate no. 22 | Conjugate no. 23 |
| --- | --- | --- | --- |
| sample no. 1 0.53 ng/ml | 113 | 67 | 86 |
| sample no. 2 5.3 ng/ml | 2380 | 1378 | 1885 |
| sample no. 3 31 ng/ml | 4175 | 2289 | 3323 |

The quantities are expressed in fluorescence units.

This Table clearly shows that the gain in fluorescence observed in conjugate 21 compared with conjugates 22 and 23 (Table 5) is also reflected in the immunoassay.

The conjugates manufactured with a cyclodextrin therefore make it possible to increase the sensitivity of the determinations in an immunoassay.

EXAMPLE 4

Manufacture of Conjugates—Importance of the Cyclodextrin

Conjugate No. 24

1 mg of ribonuclease (Ribonuclease A, ref. 5125 from SIGMA) is placed in 1 ml of 0.1 M carbonate buffer of pH 9. 3 equivalents of cyanin CY5.18 are added and the mixture is incubated at room temperature for 15 min.

The solution is then washed 6 times with 1 ml of water on Ultra free® –4 (a device from Millipore—ref. PBCC—making it possible to concentrate proteins).

The concentrate is purified on Sephadex® G25 gel and then by reversed phase HPLC.

The final molar ratio cyanin/ribonuclease is 2.5. Lines are observed at 650 and 606 nm in UV analysis. The ratio $OD_{650}/OD_{606}$ is 1.9. The appearance of the 606 nm line indicates aggregation and quenching of the ribonuclease.

Conjugate No. 25

1 mg of ribonuclease is placed in 1.5 ml of 0.1 M carbonate buffer of pH 9 containing 25% (w/v) of hydroxypropyl-β-cyclodextrin. 10 equivalents of CY5.18 are added and the mixture is incubated for 15 min at room temperature.

The solution is then concentrated and then purified on Ultra free® –4 and on Sephadex® G25 gel and then by reversed phase HPLC.

The final molar ratio cyanin/ribonuclease is 2.2.

Lines are observed at 650 and 606 nm in UV analysis. The ratio $OD_{650}/OD_{606}$ is 2.4.

The formation of a rotaxane complex with the cyclodextrin made it possible to increase the ratio $OD_{650}/OD_{606}$ and hence to reduce the aggregation phenomenon.

Conjugates no. 24 and 25 were also analyzed by MALDI/MS (Mass Laser Desorption Ionisation/Mass Spectrometry), a mild method which enables the molecular ion to be preserved by avoiding fragmentation.

Figure 2:
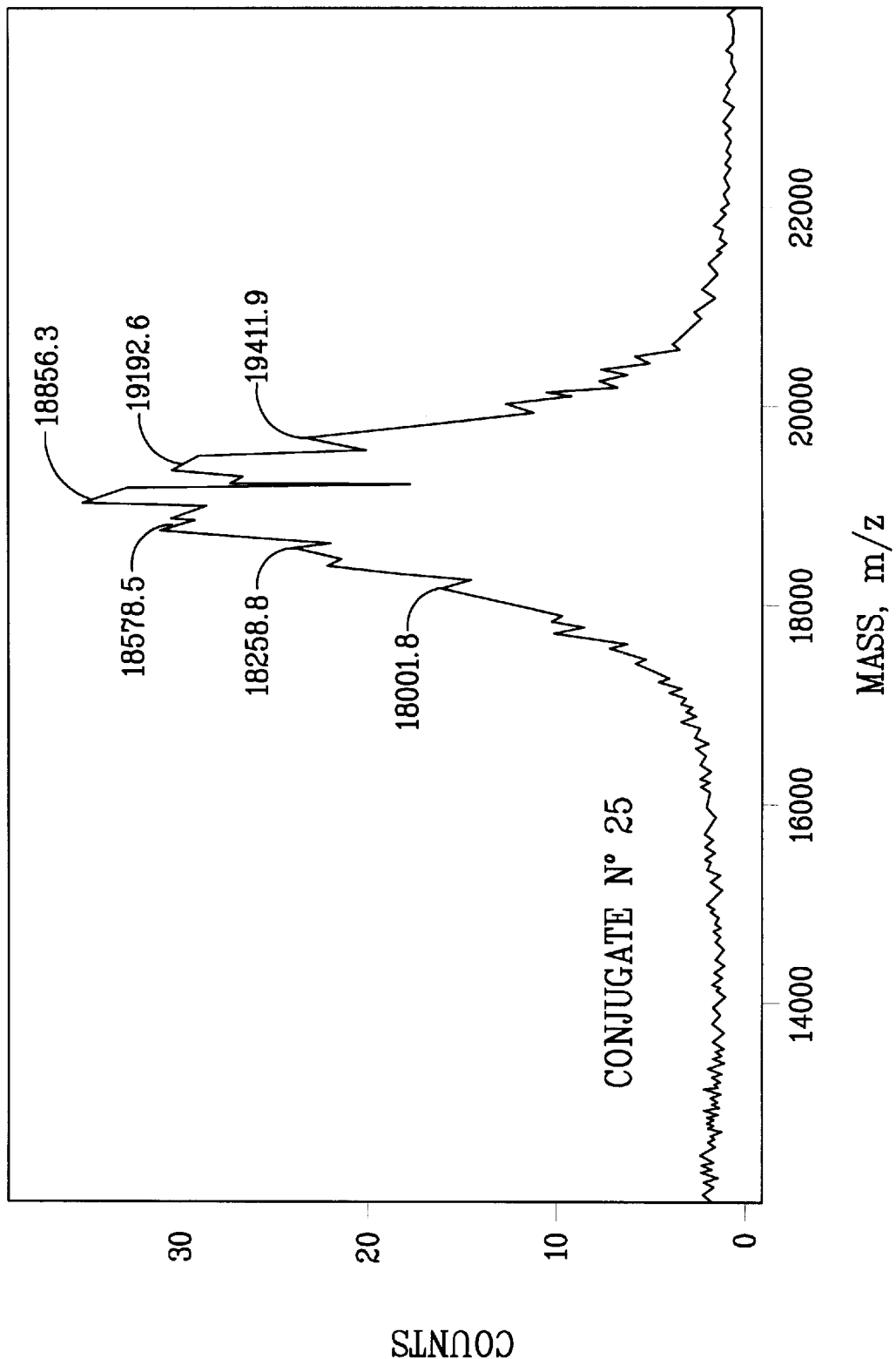
Figure 3:
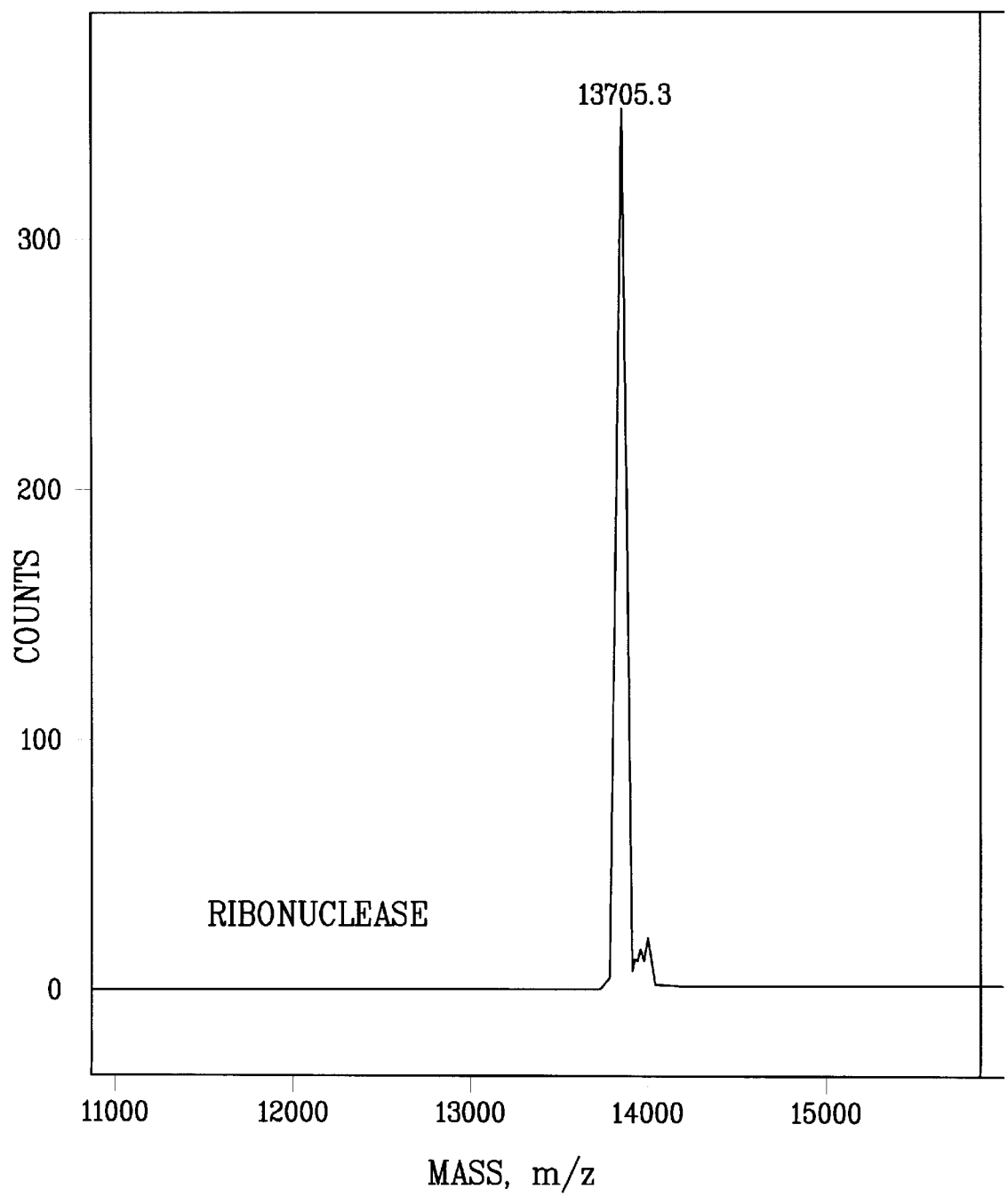

The mass spectra are shown in FIGS. 1–3 and the values of the characteristic peaks are indicated in Table 7:

TABLE 7

| Conjugate no. 24 | Conjugate no. 25 |
|---|---|
| peak at 15,018.9 | peak at 18,256.8 |
| peak at 15,647.8 | peak at 18,856.3 |
| peak at 16,287.3 | peak at 19,411.9 |

Conjugate no. 25 shows an increase in mass from 2000 to 3000 units, whereas the molar ratio cyanin/ribonuclease of conjugates 24 and 25 is identical (2.5 and 2.2).

The increase in mass of conjugate no. 25 is explained by the presence of cyclodextrin in rotaxane form.

EXAMPLE 5

Influence of the Chain Length on the Formation of the Rotaxane Complex

The following fluorescein conjugates are manufactured, one carrying a long chain on the fluorescein unit and the other carrying a short chain:

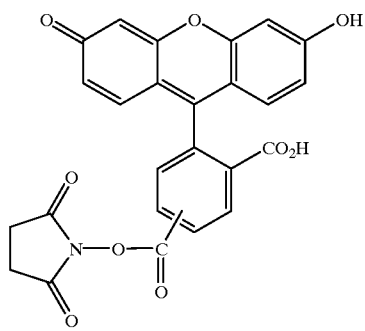

(ref. C-1311 from MOLECULAR PROBES);

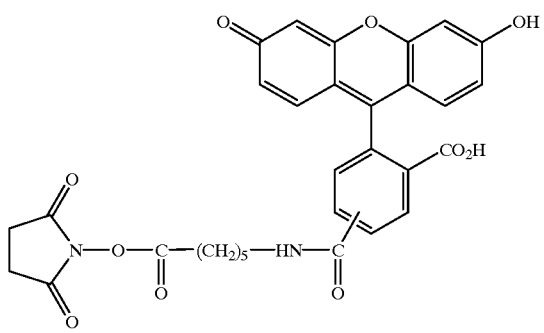

(ref. F2181 from MOLECULAR PROBES).

The conditions of manufacture of these conjugates are as follows:
- nature of the antibody: anti-HCG antibody at a concentration of 3 mg/ml
- nature of the cyclodextrin: hydroxypropyl-β-cyclodextrin at a concentration of 40% (w/v)
- 10 equivalents of fluorescein per antibody The results are indicated in Table 8:

TABLE 8

|  | Long-chain fluorescein | Short-chain fluorescein |
|---|---|---|
| final molar ratio fluorescein/antibody | 1.2 | 1.5 |
| $OD_{497}/OD_{462}$ | 2.3 | 1.8 |

The ratio $OD_{497}/OD_{462}$ of the short-chain fluorescein is markedly smaller than that of the long-chain fluorescein, proving that a long chain is necessary for complexation and for the formation of the rotaxane structure.

What is claimed is:

1. A process for the preparation of a fluorescent conjugate comprising a target molecule and a fluorophoric reagent selected from a group consisting of a cyanin, a merocyanin, a hemicyanin and a styryl compound comprising the step:
    contacting said target molecule and said fluorophoric reagent with an aqueous solution of a water soluble macrocycle containing from 1 to 40% (w/v) of said macrocycle;
    wherein said target molecule comprises at least one amino, hydroxyl, carboxyl or sulfhydryl group and said fluorophoric reagent comprises at least one functional group which reacts with said amino, hydroxyl, carboxyl or sulfhydryl group.

2. The process according to claim 1 wherein the water soluble macrocycle is an optionally substituted cyclodextrin or a calixarene substituted by hydrophilic groups.

3. The process according to claim 2 wherein the water soluble macrocycle is a cyclodextrin selected form the group consisting of α-cyclodextrin, β-cyclodextrin, γ-cyclodextrin, hydroxypropyl-α-cyclodextrin, hydroxypropyl-β-cyclodextrin, hydroxypropyl-γ-cyclodextrin, hydroxyethyl-α-cyclodextrin, hydroxyethyl-β-cyclodextrin, hydroxyethyl-γ-cyclodextrin, and 2,6-di-O-methylheptakis-β-cyclodextrin.

4. The process according to claim 1 wherein said fluorophoric reagent is a chromophore containing one or more aromatic rings and possessing a high molecular extinction coefficient.

5. The process according to claim 4 wherein said fluorophoric reagent is selected form the group consisting of a cyanin having the structure

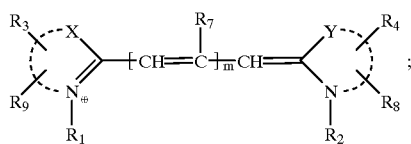

a merocyanin having the structure

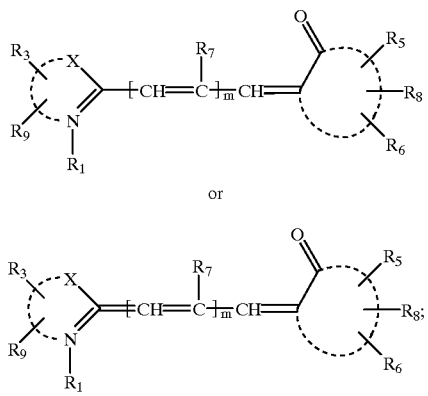

or a hemicyanin having the structure

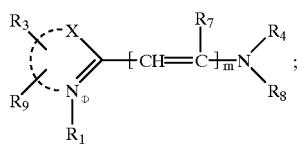

and a styryl compound having the structure

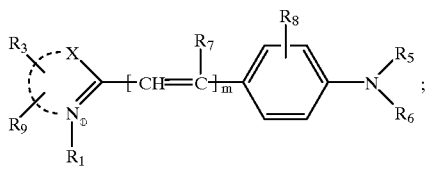

and wherein:

the broken lines in the structures each represent the carbon atoms required to form 1 to 3 fused rings, the $R_3$, $R_4$, $R_5$, $R_6$, $R_8$ and $R_9$ groups being attached to these rings;

X and Y each, independently, are N, C=O, O, S or $C(CH_3)_2$;

m is 1, 2, 3 or 4; and at least one of the groups $R_1$ to $R_7$ is capable of reacting with an amino, hydroxyl, carboxyl, or sulfhydryl group and is selected from the group consisting of

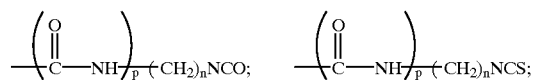 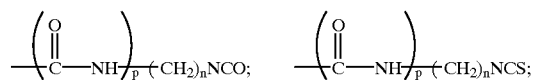

-continued

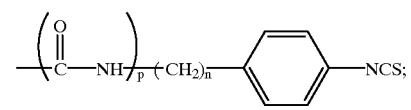

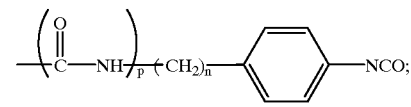

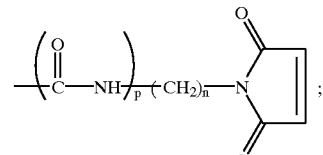

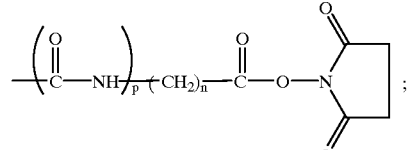

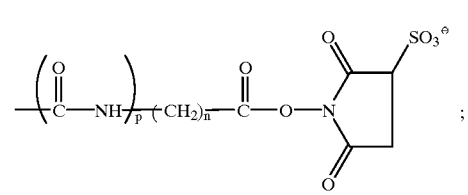

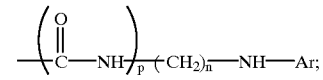

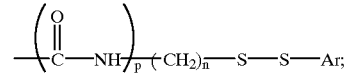

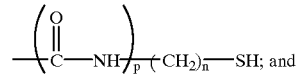

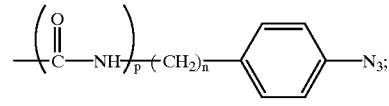

and wherein:

n is from 0 to 8;

p is 0 or 1;

Ar is a 5- or 6-membered heterocycle comprising 1 to 3 heteroatoms which is optionally substituted by a halogen atom;

those $R_1$ to $R_7$ groups which are not represented by one of the structures recited above are selected from the group consisting of a hydrogen and $—(CH_2)_r—Z$ where r is 0 to 4, and Z is $CH_3$, $SO_3H$, OH or $N^+R_1R_2R_3$, where $R_1$, $R_2$, and $R_3$ have the structures defined above, and at least one of $R_8$ and $R_9$ is $SO_3^-$ or $SO_3H$ and the other of $R_8$ and $R_9$ is hydrogen, $SO_3^-$ or $SO_3H$.

6. The process according to claim 5 wherein said fluorophoric reagent has the structure

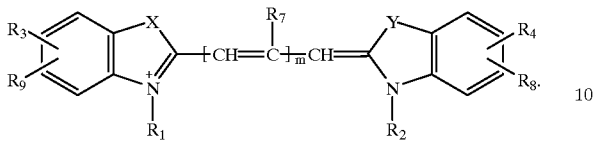

7. The process according to claim 6 wherein each of X and Y are $C(CH_3)_2$.

8. The process according to claim 7 wherein each of $R_1$ and $R_2$ are

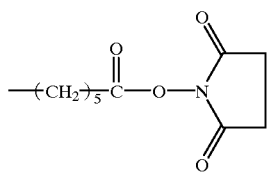

and wherein:
   $R_3$, $R_4$, and $R_7$ are each hydrogen;
   $R_8$ and $R_9$ are each $SO_3^-$; and
   m is 2.

9. The process according to claim 7 wherein $R_1$ is

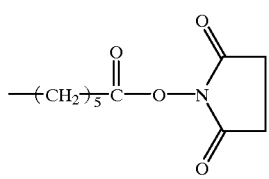

and wherein:
   $R_2$ is ethyl;
   $R_3$, $R_4$, and $R_7$ are each hydrogen;
   $R_8$ and $R_9$ are each $SO_3^-$; and
   m is 2.

10. The process according to claim 1 wherein the target molecule is an antibody, an antigen, a protein, a peptide, a hapten, a lectin, avidin, streptavidin, ribonuclease, a toxin, a carbohydrate, an oligosaccharide, a polysaccharide, a nucleic acid, a hormone, or a drug.

11. A fluorescent conjugate obtained by the process according to claim 1.

12. A fluorescent conjugate according to claim 11 wherein said conjugate is produced by attachment of the inclusion complex formed by said water-soluble macrocycle and said fluorophoric reagent to said target molecule.

13. A fluorescent conjugate according to claim 12 wherein said inclusion complex remains in the final structure of the conjugate and forms a stable rotaxane.

14. A process for the preparation of a fluorescent conjugate comprising a target molecule and a fluorophoric reagent selected from a group consisting of a cyanin, a merocyanin, a hemicyanin and a styryl compound comprising the step:
   contacting said target molecule and said fluorophoric reagent with an aqueous solution of a calixarene containing from 1 to 40% (w/v) of said calixarene;

wherein said target molecule comprises at least one amino, hydroxyl, carboxyl or sulfhydryl group and said fluorophoric reagent comprises at least one functional group which reacts with said amino, hydroxyl, carboxyl or sulfhydryl group; and wherein said calixarene comprises the structure

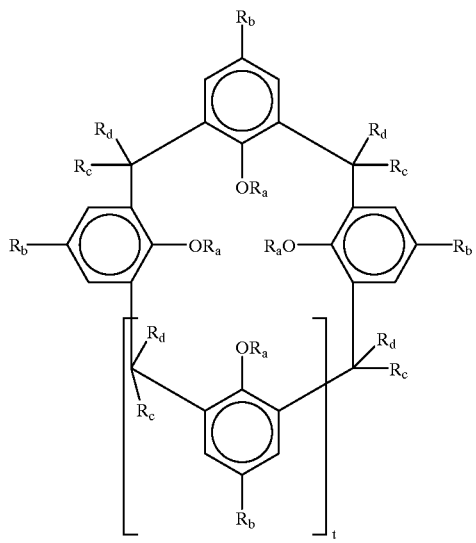

and wherein:
   $R_a$ and $R_b$ each, independently, are a hydrophilic group selected from the group consisting of H, $(CH_2)_pCO_2H$, $(CH_2)_pOH$, $(CH_2)_pNH_2$, $(CH_2)_pSO_3H$, and $(CH_2)_pN^+R_cR_dR_e$;
   $R_c$, $R_d$, and $R_e$ are each, independently, hydrogen or a $C_1$–$C_3$ alkyl;
   p is 0 to 4 for $R_b$ and 1 to 4 for $R_a$; and
   t is 1 to 5.

15. The process according to claim 14 wherein said fluorophoric reagent is a chromophore containing one or more aromatic rings and possessing a high molecular extinction coefficient.

16. The process according to claim 15 wherein said fluorophoric reagent is selected form the group consisting of a cyanin having the structure

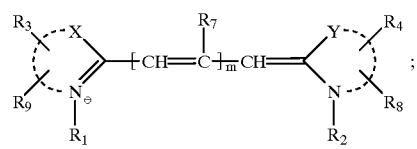

a merocyanin having the structure

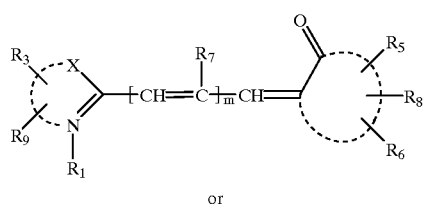

or

-continued

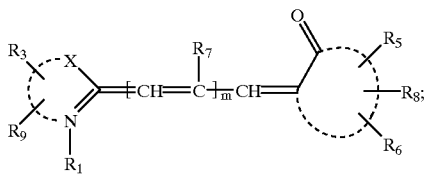

a hemicyanin having the structure

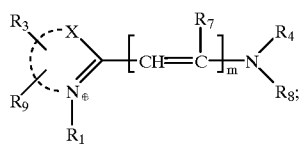

and a styryl compound having the structure

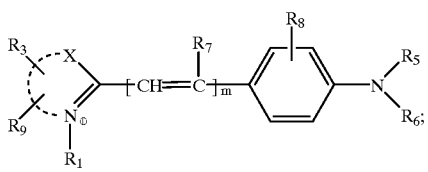

and wherein:
the broken lines in the structures each represent the carbon atoms required to form 1 to 3 fused rings, the $R_3$, $R_4$, $R_5$, $R_6$, $R_8$ and $R_9$ groups being attached to these rings;
X and Y each, independently, are N, C=O, O, S or $C(CH_3)_2$;
m is 1, 2, 3 or 4; and
at least one of the groups $R_1$ to $R_7$ is capable of reacting with an amino, hydroxyl, carboxyl, or sulfhydryl group and is selected from the group consisting of

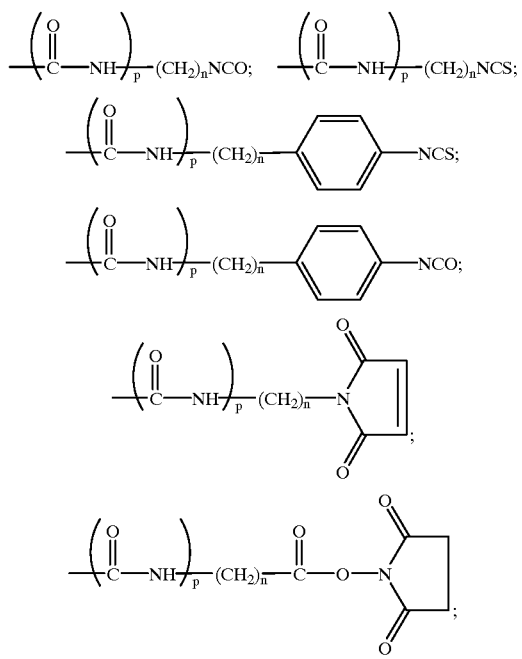

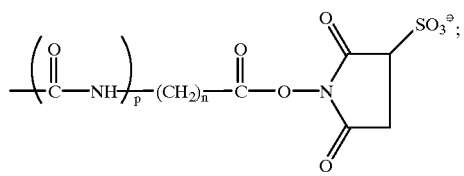

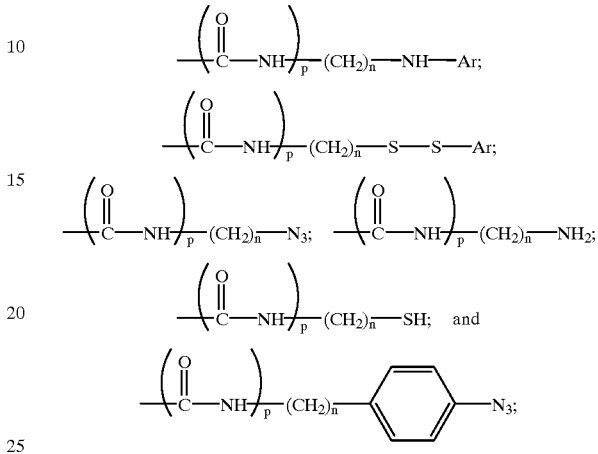

and wherein:
n is from 0 to 8;
p is 0 or 1;
Ar is a 5- or 6-membered heterocycle comprising 1 to 3 heteroatoms which is optionally substituted by a halogen atom;
those $R_1$ to $R_7$ groups which are not represented by one of the structures recited above are selected from the group consisting of a hydrogen and $—(CH_2)_r—Z$ where r is 0 to 4, and Z is $CH_3$, $SO_3H$, OH or $N^+R_1R_2R_3$, where $R_1$, $R_2$, and $R_3$ have the structures defined above, and at least one of $R_8$ and $R_9$ is $SO_3^-$ or $SO_3H$ and the other of $R_8$ and $R_9$ is hydrogen, $SO_3^-$ or $SO_3H$.

17. The process according to claim 16 wherein said fluorophoric reagent has the structure

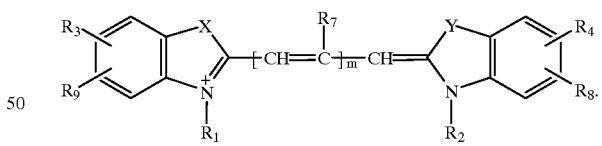

18. The process according to claim 17 wherein each of X and Y are $C(CH_3)_2$.

19. The process according to claim 18 wherein each of $R_1$ and $R_2$ are

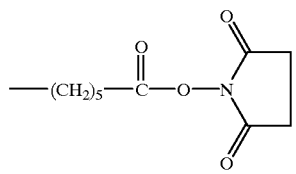

and wherein:
 $R_3$, $R_4$, and $R_7$ are each hydrogen;
 $R_8$ and $R_9$ are each $SO_3^-$; and
 m is 2.

20. The process according to claim 18 wherein $R_1$ is

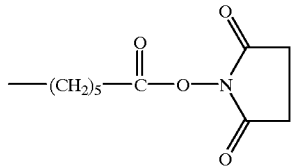

and wherein:
 $R_2$ is ethyl;
 $R_3$, $R_4$, and $R_7$ are each hydrogen;
 $R_8$ and $R_9$ are each $SO_3^-$; and
 m is 2.

21. The process according to claim 14 wherein the target molecule is an antibody, an antigen, a protein, a peptide, a hapten, a lectin, avidin, streptavidin, ribonuclease, a toxin, a carbohydrate, an oligosaccharide, a polysaccharide, a nucleic acid, a hormone, or a drug.

22. A fluorescent conjugate obtained by the process according to claim 14.

23. A fluorescent conjugate according to claim 22 wherein said conjugate is produced by attachment of the inclusion complex formed by said water-soluble calixarene and said fluorophoric reagent to said target molecule.

24. A fluorescent conjugate according to claim 23 wherein said inclusion complex remains in the final structure of the conjugate and forms a stable rotaxane.

* * * * *